(12) United States Patent
Hansen

(10) Patent No.: US 11,752,029 B2
(45) Date of Patent: Sep. 12, 2023

(54) ADJUSTABLE, WATERPROOF WOUND SHIELD

(71) Applicant: Michael Quiz Hansen, Highland, UT (US)

(72) Inventor: Michael Quiz Hansen, Highland, UT (US)

( * ) Notice: Subject to any disclaimer, the term of this patent is extended or adjusted under 35 U.S.C. 154(b) by 765 days.

(21) Appl. No.: 16/705,823

(22) Filed: Dec. 6, 2019

(65) Prior Publication Data
US 2020/0179155 A1   Jun. 11, 2020

Related U.S. Application Data

(60) Provisional application No. 62/776,744, filed on Dec. 7, 2018.

(51) Int. Cl.
*A61F 13/00*   (2006.01)
*A61F 5/449*   (2006.01)
*A61F 5/445*   (2006.01)

(52) U.S. Cl.
CPC .............. *A61F 5/449* (2013.01); *A61F 5/445* (2013.01); *A61F 13/00034* (2013.01); *A61F 2013/00165* (2013.01); *A61F 2013/00217* (2013.01); *A61F 2013/00268* (2013.01)

(58) Field of Classification Search
USPC ........ 128/888, 889; 602/79; 24/578.13, 302, 24/578, 13
See application file for complete search history.

(56) References Cited

U.S. PATENT DOCUMENTS

| | | | | |
|---|---|---|---|---|
| 2,367,690 | A * | 1/1945 | Purdy | A61F 15/006 128/888 |
| 6,274,787 | B1 * | 8/2001 | Downing | A61F 15/008 602/14 |
| 7,628,767 | B1 * | 12/2009 | Simmons | A61F 15/004 128/850 |
| 8,558,050 | B2 * | 10/2013 | Aali | A61F 13/00068 604/289 |
| 2010/0081983 | A1 * | 4/2010 | Zocher | A61F 15/008 602/54 |
| 2015/0209238 | A1 * | 7/2015 | Kurz | A61M 19/00 128/890 |
| 2018/0296405 | A1 * | 10/2018 | Raymond-Coblantz | A61F 13/0233 |

\* cited by examiner

*Primary Examiner* — Kim M Lewis
(74) *Attorney, Agent, or Firm* — David B. Tingey; Bryant J. Keller; Kirton McConkie

(57) ABSTRACT

An apparatus for protecting a wound. The apparatus includes a waterproof shield element to cover a wound area of a user's body, where the elevated top surface of the shield element is elevated away from the user's body. A retention mechanism selectively retains the shield element against the user's body, utilizing the elevated top surface to create a normal force between the shield element and the user's body to thereby form an effective seal between the shield element and the user's body.

17 Claims, 10 Drawing Sheets

ADJUSTABLE, WATERPROOF WOUND SHIELD

BACKGROUND

Field of the Invention

This invention relates to protective medical devices and shields.

Background of the Invention

Ostomy surgery is a life-saving procedure that allows bodily waste to pass through a surgically created stoma on the abdomen. Waste then empties into a prosthetic known as a 'pouch' or 'ostomy bag' on the outside of the body.

Normal exposure to air or water will not hurt the stoma. An ostomy pouch may therefore be removed for showering or bathing. Often, however, removing the pouch may be impractical or inconvenient. In such cases, it may be desirable to temporarily cover the area with plastic or other waterproof covering.

What is needed is a waterproof wound covering that is simple and convenient to use to shield an ostomy pouch from exposure to moisture. Also what is needed is a waterproof wound covering that effectively and reliably seals the wound covering against the user's skin. Ideally, such a wound covering would be easy to adjust to a particular user, comfortable, inexpensive, and reusable.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

Embodiments of the invention may provide an adjustable, waterproof shield to protect a wound, ostomy pouch or other medical device from injury, damage and/or exposure to water. The shield may be constructed of sturdy, reusable materials that are inexpensive to procure and simple to manufacture. The shield may also include features rendering it substantially impervious to moisture and comfortable for a user to wear. Other features may enable the shield to be easily adjusted to accommodate various sizes of users.

Figure 1:
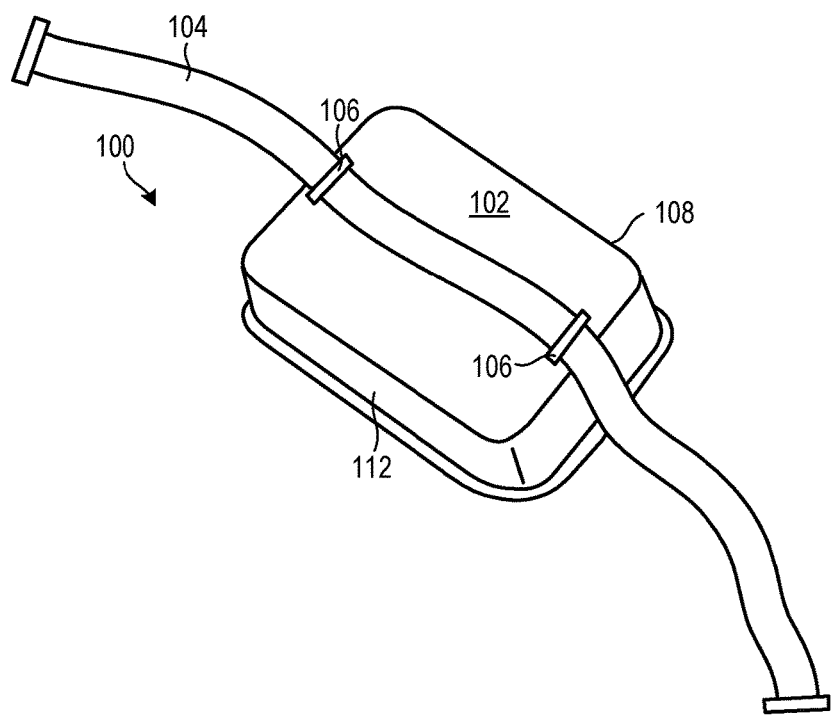
FIG. 1 is a perspective view of one embodiment of an apparatus for protecting a wound in accordance with the invention.

Referring now to FIG. 1, some embodiments of an apparatus 100 in accordance with the invention may include a waterproof shield element 102 having dimensions sufficient to cover a wound area of a user's body. In certain embodiments, the shield element 102 may include an elevated top surface 108 that is suspended substantially above the wound area by one or more sidewalls 112. In one embodiment, one or more of the sidewalls 112 may extend substantially perpendicularly from the elevated top surface 108 of the shield element 102. The sidewalls 112 may ensure that the elevated top surface 108 resides at a particular height or distance from the user's body. In certain embodiments, for example, the elevated top surface 108 may reside at a height of at least one centimeter away from the user's body. In other embodiments, the elevated top surface 108 may reside at a height of at least two centimeters or at least three centimeters away from the user's body.

In any case, the shield element 102 may be substantially rigid to maintain the elevated top surface 108 at a predetermined height or distance away from the user's body. To this end, the elevated top surface 108 and/or sidewalls 112 may be fabricated from materials such as polycarbonate, polyethylene, polypropylene, thermoplastic elastomer ("TPE"), or other such materials or combination of materials known to those in the art. The materials used to construct the shield element 102 may be substantially impervious to water and other liquids to ensure that a wound area of user's body is not exposed to liquid or other moisture when environmentally present. In some embodiments, the shield element 102 may be treated, or a waterproof coating may be applied thereto, to render the shield element 102 substantially waterproof.

The shield element 102 may further include a retention mechanism 104, such as an adjustable strap, belt or band, to retain the shield element 102 against a user's abdomen, extremity, or other area of the body. The retention mechanism 104 may utilize the elevated top surface 102 of the shield element 102 to create a normal force between the shield element 102 and the user's body, thereby creating an effective seal between the shield element 102 and the user's body. In certain embodiments, the retention mechanism 104 may include, for example, a substantially flexible or deformable material or fabric such as a material or fabric containing nylon, polyester, thermoplastic elastomer ("TPE"), composite webbing, or the like.

In certain embodiments, the shield element 102 may further include an attachment mechanism 106 to selectively secure a position of the retention mechanism relative 104 to the shield element 102. In some embodiments, the attachment mechanism 106 may include a slot, a slide-in connector, a clip, a clasp, a buckle, a guide, or other such component known to those in the art to selectively secure at least a portion of the retention mechanism 104 relative to the shield element 102. The attachment mechanism 106 may be coupled to or integrated with the shield element 102. In one embodiment, the attachment mechanism 106 may be coupled to or integrated with the elevated top surface 108 such that the retention mechanism 104 is maintained in a position to create a normal force between the shield element 102 and the user's body.

In certain embodiments, the attachment mechanism 106 may simply retain the retention mechanism 104 in a substantially fixed position relative to the shield element 102. For example, the attachment mechanism 106 may include one or more suspended bars attached to the shield element 102 such that the retention mechanism 104 may be threaded under the bars and retained thereby.

In some embodiments, the attachment mechanism 106 may be coupled to or associated with the retention mechanism 104 rather than the shield element 102. For example, in one embodiment, the retention mechanism 104 may include an adhesive or other such attachment mechanism 106 configured to selectively attach to a surface of the shield element 102. In other embodiments, the attachment mechanism 106 may be coupled to the retention mechanism 104 to enable the retention mechanism 104 to be secured to itself and thereby retain a substantially fixed position relative to the shield element 102. An end of the retention mechanism 104, for example, may include a fastener, clip, or other mechanical connecting device to connect to a receiving portion on an opposite end of the retention mechanism 104.

In any case, the retention mechanism 104 may utilize the shield element 102 to create a normal force between the shield element 102 and the user's body 200, thereby forming an effective seal between the shield element 102 and the user's body 200. A height 212 of the elevated top surface 108 relative to the user's body 200 may create an angle 206 between the retention mechanism 104 and the shield element 102. The retention mechanism 104 may exert a force 208 on the shield element 102 at this angle 206. This force 208 may be broken into a force 210*a* that is substantially lateral to the user's body 200 and a force 210*b* that is substantially normal to the user's body 200. The greater the height 212 of the shield element, the smaller the angle 206 and the larger the normal force 210*b*. The larger the normal force 210*b*, the better the seal between the retention mechanism 104 and the user's body 200. Without sufficient height 212, most of the force 208 will be lateral force 210*a*, which will not assist in creating a seal between the shield element 102 and the user's body 200.

In some embodiments the height 212 may be at least one centimeter, at least two centimeters, or at least three centimeters away from the user's body 200. The height 212 may be selected to accommodate any projection of the wound area 202, as well as to create a desired normal force 210*b* between the shield element 102 and the user's body 200. The sidewalls 112 may maintain the elevated top surface 108 at a substantially constant height 212 such that the elevated top surface 108 may be suspended outwardly from the user's body 200 while maintaining a normal force 210*b* directed inwardly towards the user's body 200.

Figure 2:
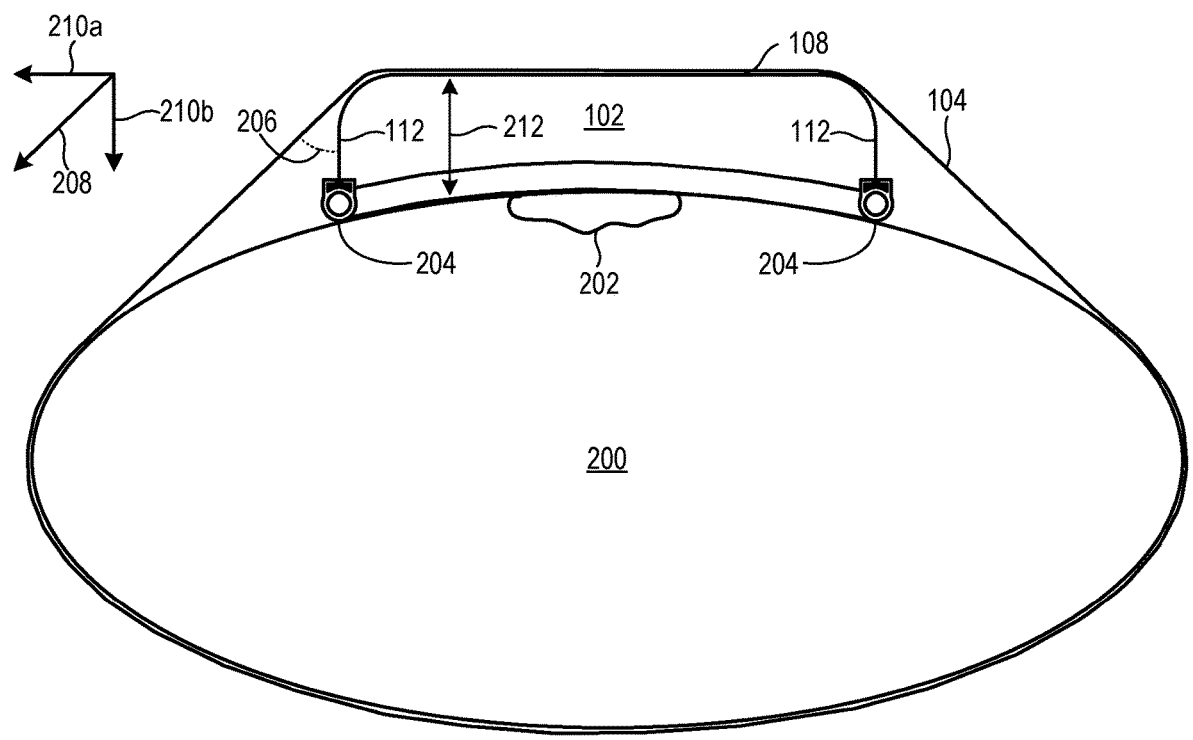
FIG. 2 is a cross-sectional view of a user's body wearing an embodiment of an apparatus for protecting a wound in accordance with the invention.

Referring now to FIG. 2, the shield element 102 may be applied to cover a wound area 202 of a user's body 200. In certain embodiments, the shield element 102 may be provided in a variety of sizes and/or shapes, including round, oval, rectangular, or irregular. In certain embodiments, a height 212 of the elevated top surface 102 of the shield element 102 may be adjustable to accommodate, for example, an ostomy protrusion. For example, one or more sidewalls 112 of the shield element 102 may include an accordion-like formation to enable the elevated top surface 102 to be raised or lowered to customize a fit of the shield element 102 relative to the wound area 202. A size and/or shape of the shield element 102 may be selected such that the outer edges 204 of the shield element 102 may be situated outside the wound area 202.

In certain embodiments, the retention mechanism 104 may also be adjustable to accommodate a variety of user body 200 sizes. In one embodiment, for example, the retention mechanism 104 may include a substantially flexible strap that may be extended over the shield element 102 and around a circumference of the user's body 200. An end of the flexible strap may be secured relative to the shield element 102 to maintain application of a normal force between the shield element 102 and the user's body 200. The end of the flexible strap may be secured by, for example, a hook and loop closure, Velcro®, a button, a snap, or any other such means known to those in the art.

A length of the substantially flexible strap may be adjusted as needed to retain the shield element 102 against the user's body 200. The length of the flexible strap may be further adjusted to vary an amount of tension applied to the user's body 200, as well as a normal force between the shield element 102 and the user's body 200.

In any case, application of the retention mechanism 104 may create a normal force between the shield element 102 and the user's body 200 sufficient to form an effective seal between the shield element 102 and the user's body 200. In certain embodiments, the retention mechanism 104 may be extended across at least a portion of the elevated top surface 102 of the shield element 102 to create the normal force between the shield element 102 and the user's body 200.

Figure 3:
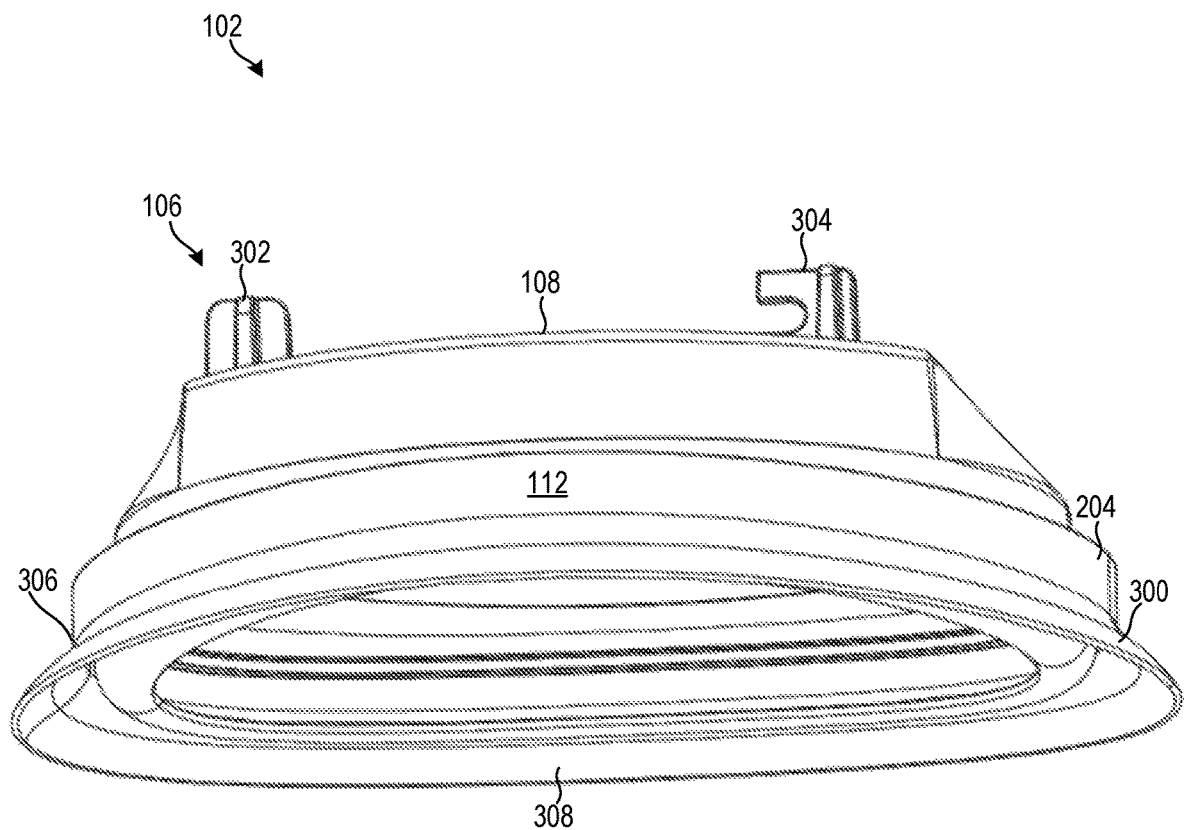
FIG. 3 is a bottom perspective view of a shield element in accordance with certain embodiments of the invention.
Figure 4:
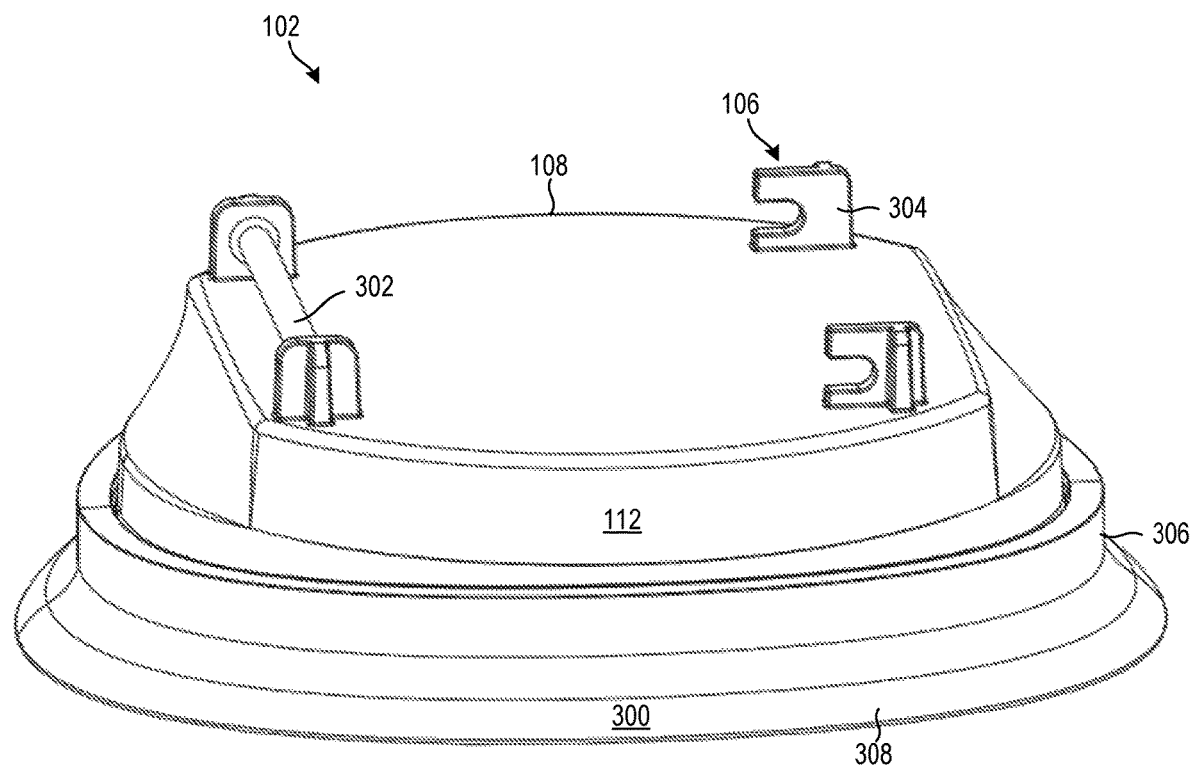
FIG. 4 is a top perspective view of the shield element of FIG. 3.

Referring now to FIGS. 3 and 4, certain embodiments of a shield element 102 may include an attachment mechanism 106 integrated with the elevated top surface 108 to secure a position of the retention mechanism 104 relative to the shield element 102. As shown, in one embodiment, the attachment mechanism 106 may include an attachment element 302 to retain a first end of a retention mechanism 104, such as a flexible strap, and a securing element 304 to retain a second end of the retention mechanism 104.

The first end of the retention mechanism 104 may engage the attachment element 302 by, for example, wrapping around the rod portion of the attachment element 302 and connecting back to itself via, for example, a hook and loop closure, Velcro®, a button, a snap, or any other such means known to those in the art. The second end of the retention mechanism 104 may then be secured to the shield element 102 via the securing element 304. The securing element 304 may include, for example, a feature substantially corresponding to a component attached to or integrated with the second end of the retention mechanism 104 such that the second end of the retention mechanism 104 may be received and secured by the securing element 304 via a press fit, a clasp, a buckle, or any other such means known to those in the art.

In some embodiments, the shield element 102 may further include a seal element 300 coupled to or integrated with at least a portion of a lower edge 306 of the shield element 102. The seal element 300 may include, for example, a rubber, plastic, or other such gasket having features to interlock or mate with the lower edge 306 of the shield element 102. Alternatively, the seal element 300 be attached to the lower edge 306 of the shield element 102 by an adhesive, press fit, mechanical elements, or any other means known to those in the art. The seal element 300 may include flexible fins 308 or projections along its outer surface to deflect in response to pressure against a user's body 200.

Figure 5:
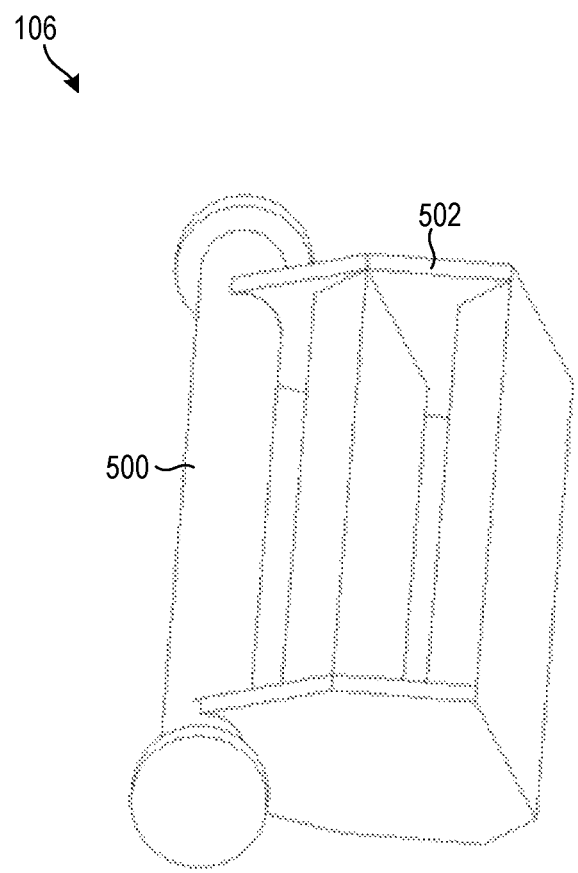
FIG. 5 is a perspective view of a fastening component and adjustment mechanism in accordance with one embodiment of the invention.
Figure 6:
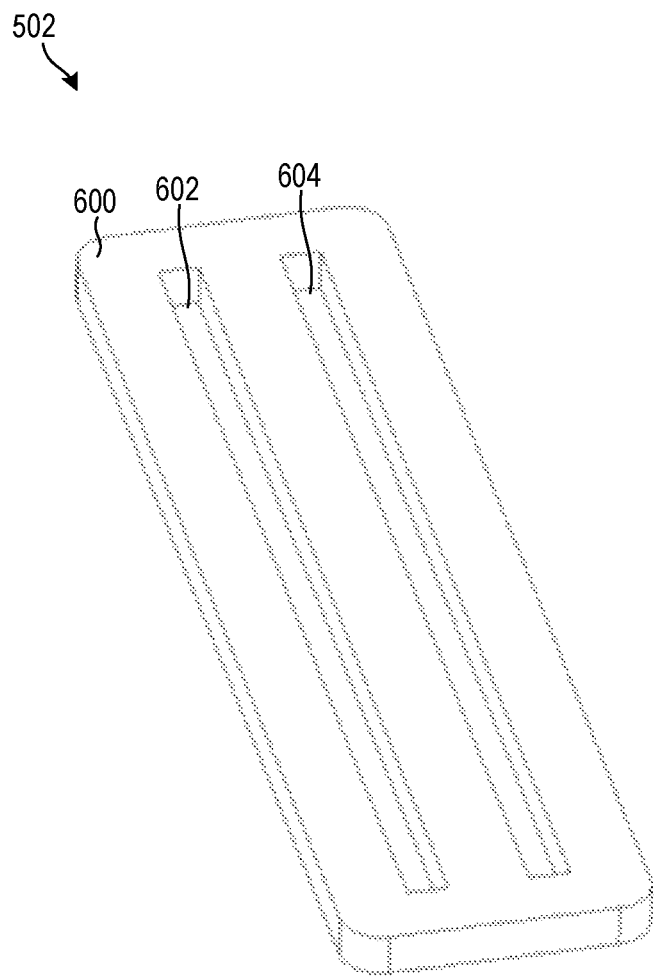
FIG. 6 is a perspective view of an adjustment mechanism in accordance with another embodiment of the invention.

Referring now to FIGS. 5 and 6, in some embodiments the attachment mechanism 106 may include a securing element 304 to engage a fastening component 500 coupled to or integrated with an end of the retention mechanism 104. As shown in FIG. 5, for example, the fastening component 500 may include a rod or pin configured to mate with a securing element 304 attached to or integrated with the shield element 102. In certain embodiments, the fastening component 500 may include an adjustment mechanism 502 to facilitate adjusting a length and/or force applied by the retention mechanism upon securing the retention mechanism 104 to the shield element 102. The fastening component 500 and adjustment mechanism 502 may be a single monolithic structure or may be independent components.

In certain embodiments, as shown in FIG. 5, the fastening component 500 and the adjustment mechanism 502 may be selectively joined together, by, for example, a press fit. Alternatively, as shown in FIG. 6, the adjustment mechanism 502 may be entirely independent of the fastening component 500. As shown in FIGS. 5 and 6, the adjustment mechanism 502 may include a slider 600 to receive at least a portion of a retention mechanism 104, such as a flexible strap. As known to those in the art, the strap may be received into a first slot 602 of the slider 600 and pulled through a second slot 604 of the slider 600 to adjust a length and/or tautness of the strap relative to the shield element 102. In any case, the slider 600 or other adjustment mechanism 502 may maintain the retention mechanism 104 in a substantially flat position relative to the shield element 102 to facilitate a user's comfort as well as to avoid interference with any clothing applied over the apparatus 100.

Referring now to FIGS. 7-11, as previously mentioned, the shield element 102 may further include a seal element 300 coupled to or integrated with at least a portion of a lower edge 306 of the shield element 102. The seal element 300 may comprise a material that is substantially impervious to liquid or moisture, such as rubber or plastic. The seal element 300 may also be dimensioned and oriented to achieve a maximum seal between the shield element 102 and the user's body 200, thereby preventing moisture from entering the wound area 202. In some embodiments, the lower edge 306 of the shield element 102 and/or the seal element 300 may be flat, or may be curved or contoured to substantially conform to a shape of the user's body 200.

The seal element 300 may also be substantially flexible to provide a comfortable interface between the shield element 102 and the user's body 200. In some embodiments, the seal element 300 may be constructed of a substantially flexible material such as foam, rubber, plastic, composite, or the like. In some embodiments, a substantially waterproof coating or treatment may be applied to the seal element 300 to further prevent moisture from coming into contact with the wound area 202, medical device, or other sensitive area or component protected by the shield element 102. In certain embodiments, the seal element 300 may be sufficiently flexible to substantially conform to contours of the user's body 200 while maintaining a reliable seal between the seal element 300 and the user's body 200.

Figure 11:
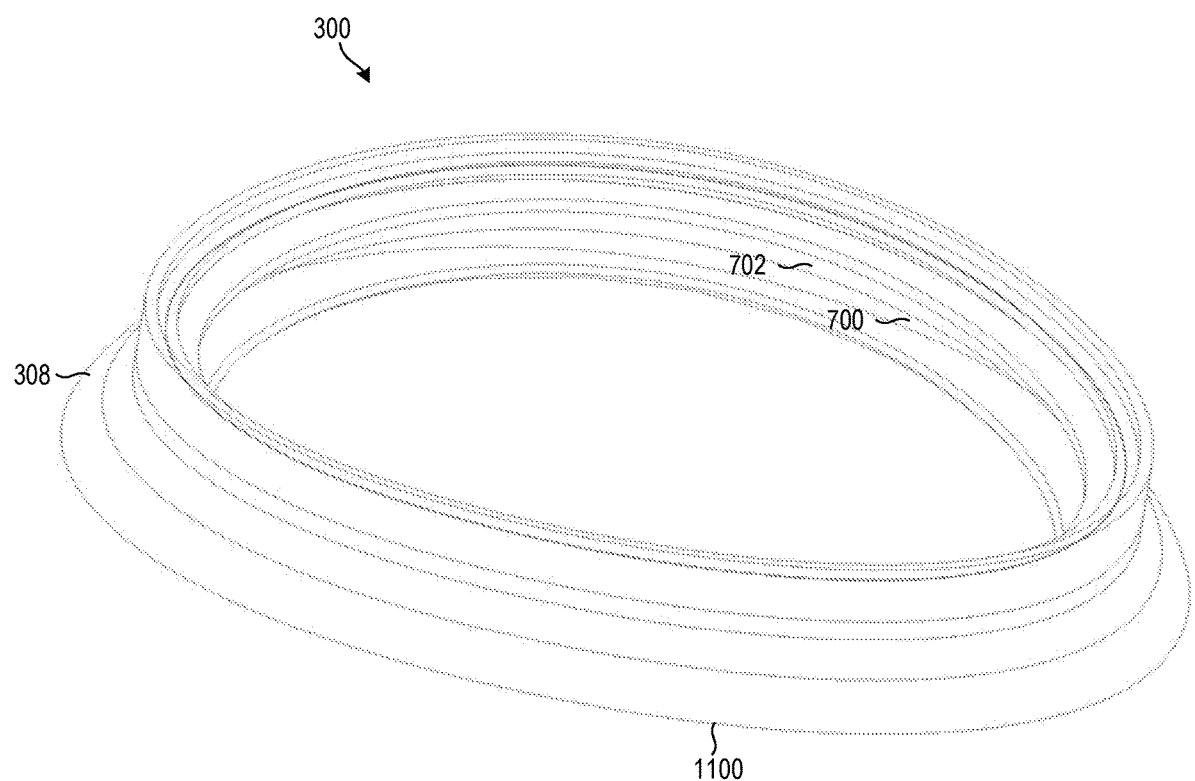
FIG. 11 is a perspective view of a seal element in accordance with certain embodiments of the invention.

As shown in FIG. 11, in one embodiment, the seal element 300 may include substantially cylindrical tubing or a cylindrical gasket attached to the lower edge 306 of the shield element 102. Of course, the seal element 300 may also include any regular or irregular shape or cross-section known to those in the art. In other embodiments, for example, the seal element 300 may include a substantially flat or planar fin 308, a combination of tubing and fins 308, or may take any other form known to those in the art to substantially seal a junction between the shield element 102 and the user's body 200.

Figure 10:
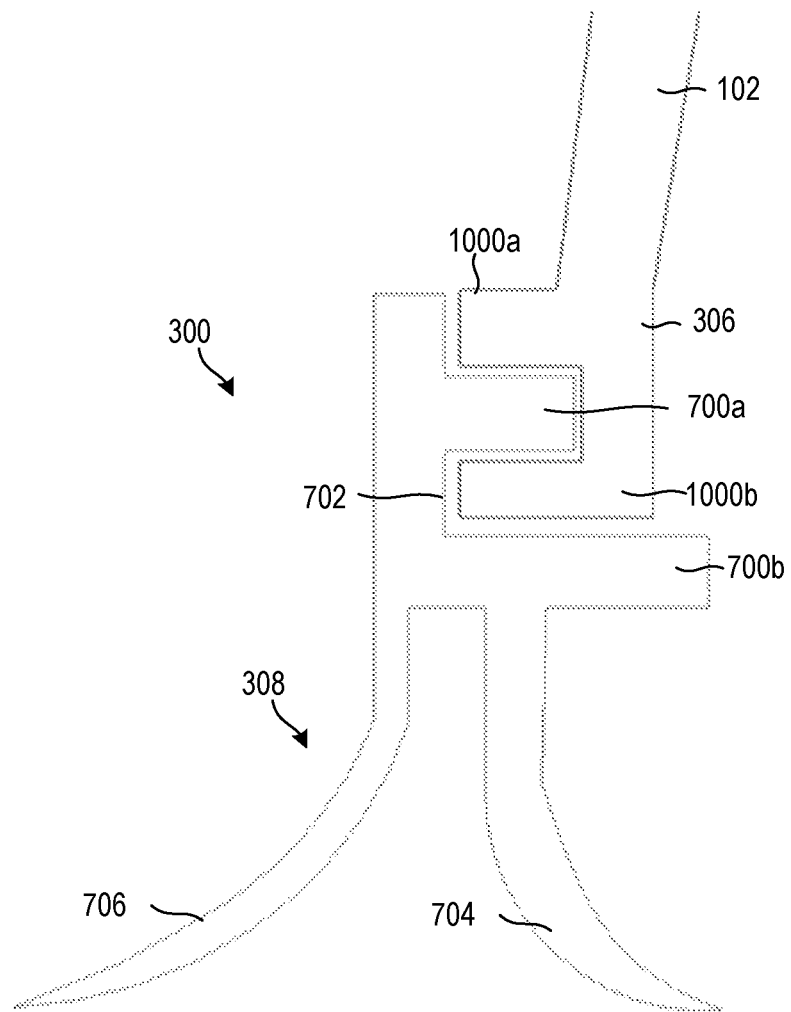
FIG. 10 is a side cross-sectional view of a fourth embodiment of a seal element coupled to a wound shield in accordance with the invention.

In some embodiments, the seal element 300 may include one or more projections 700 and/or cutouts 702 or indentations to mate with corresponding features of the lower edge 306 of the shield element 102. In this manner, the seal element 300 may be removably attached to the shield element 102, while creating a reliable seal relative thereto. Referring now to FIG. 10, in one embodiment, the seal element 300 may include two projections 700a, 700b having sizes and shapes corresponding to ridges 1000a, 1000b in the shield element 102. Cutouts 702 in the seal element 300 created by the projections 700a, 700b, may engage ridges 1000b of the shield element 102, thereby reliably joining the shield element 102 to the seal element 300.

In certain embodiments, the seal element 300 may further include one or more flexible fins 308 or projections along its perimeter 1100 to seal an interface between the seal element 300 and the user's body 200. At least one fin 308 may deflect against the contours of a user's body 200 to create a reliable seal between the seal element 300 and the user's body 200, as well as to facilitate user comfort.

Figure 7:
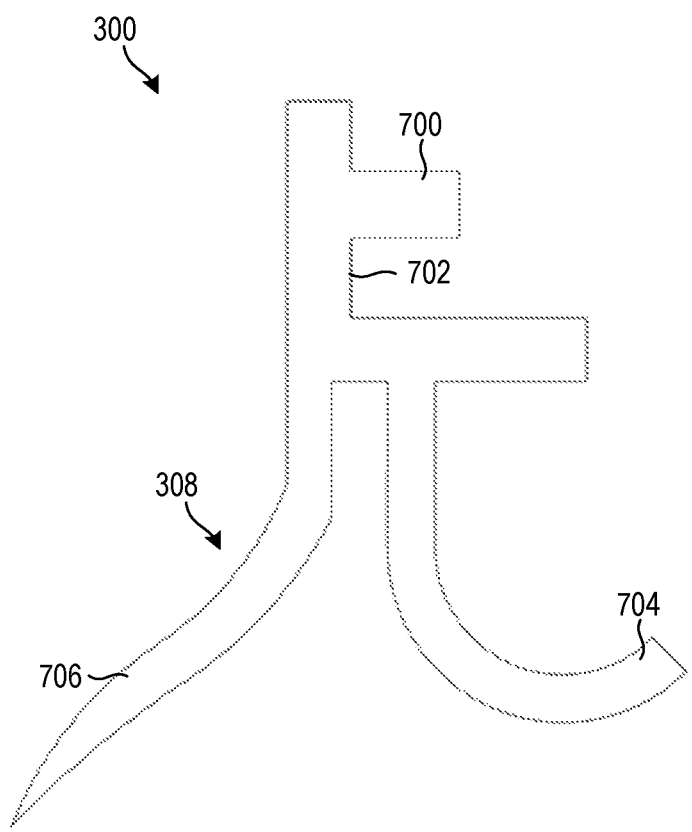
FIG. 7 is a side cross-sectional view of one embodiment of a seal element in accordance with the invention.
Figure 8:
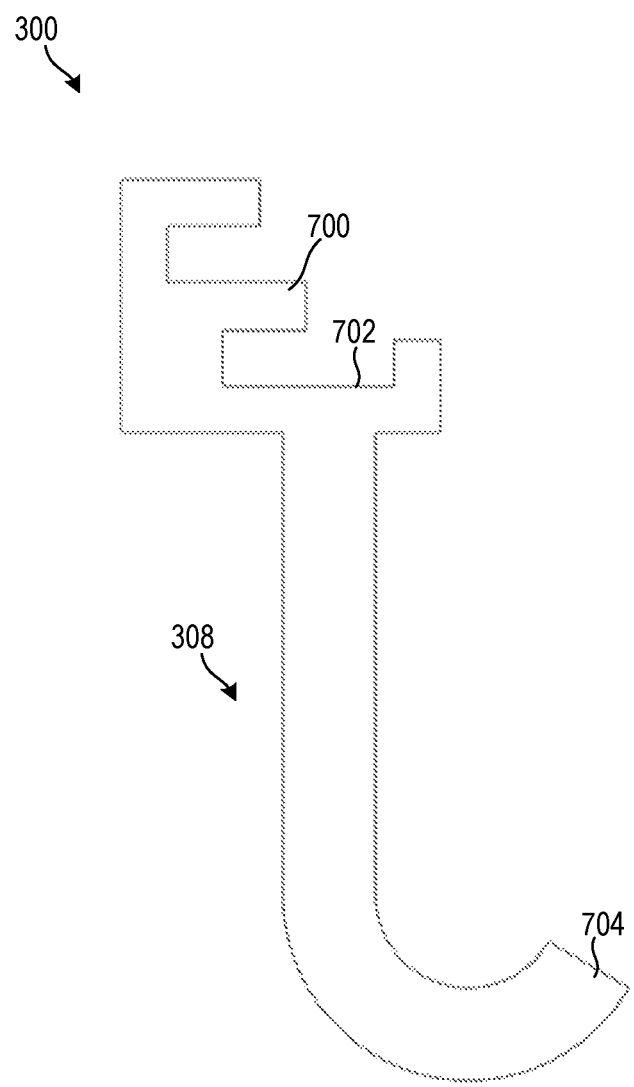
FIG. 8 is a side cross-sectional view of a second embodiment of a seal element in accordance with the invention.
Figure 9:
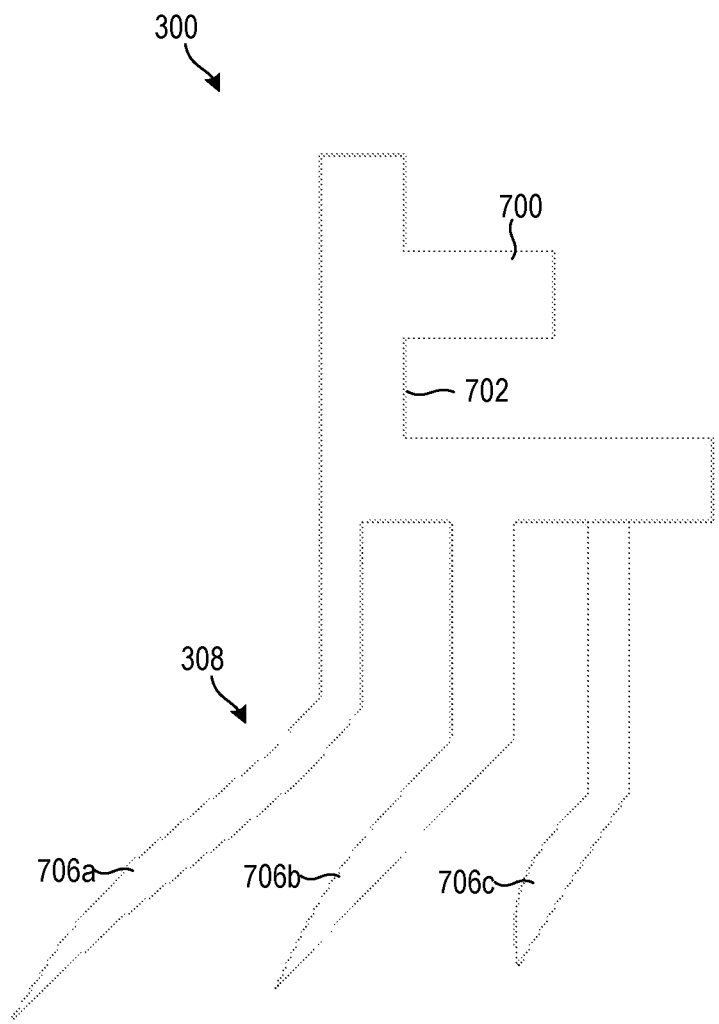
FIG. 9 is a side cross-sectional view of a third embodiment of a seal element in accordance with the invention.

Certain embodiments of the invention may include a plurality of fins 308 oriented in varying or opposing directions, thus further ensuring a reliable seal between the seal element 300 and the user's body 200. As shown in FIGS. 7 and 10, for example, one fin 704 may be situated to deflect inwardly towards the wound area 202, while another fin 706 may be situated to deflect outwardly towards an unprotected area of the user's body 200. In other embodiments, as shown in FIG. 8, a single fin 704 may be provided to deflect inwardly towards the wound area 202. In still other embodiments, as shown in FIG. 9, a plurality of fins 706a, 706b, 706c may be oriented such that they deflect in the same direction in series, thereby providing multiple layers of protection. Of course, any number of fins 308 in any combination, variation, and/or orientation is possible and contemplated herein.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. An apparatus for protecting a wound, the apparatus comprising:
   a waterproof shield element to cover a wound area of a user's body, the waterproof shield element comprising an elevated top surface that is configured to be elevated away from the user's body during use;
   a seal element coupled to a lower portion of the waterproof shield element, wherein the seal element comprises at least one of:
   (i) a base portion that is coupled to the lower portion of the waterproof shield element, wherein a first end portion of a flexible elongated projection is coupled to the base portion such that a second end of the flexible elongated projection extends away from the base portion of the seal element and away from the lower portion of the waterproof shield element and towards a center of a cavity defined by the waterproof shield element such that the second end of the flexible elongated projection is configured to extend between the base portion of the seal element and the user's body when the waterproof shield element covers the wound area of the user's body; and
   (ii) at least two projections that each extend away from the lower portion of the waterproof shield element and that each have a respective terminal portion that is configured to contact the user's body during use; and
   a retention mechanism to selectively retain the waterproof shield element against the user's body during use, the retention mechanism being configured to create, during use, a force between the waterproof shield element and the user's body to form an effective seal between the seal element and the user's body.

2. The apparatus of claim 1, further comprising an attachment mechanism to selectively secure a position of the retention mechanism relative to the waterproof shield element, wherein the retention mechanism comprises a flexible strap that is adjustably coupled to an elongated member having a longitudinal axis that runs orthogonal to a length of the flexible strap,
   wherein a recess is defined in the attachment mechanism, and
   wherein the recess is configured to selectively catch the elongated member.

3. The apparatus of claim 2, wherein the attachment mechanism comprises a securing element that defines the recess and that is coupled to the elevated top surface.

4. The apparatus of claim 2, wherein the seal element comprises the flexible elongated projection that extends away from the lower portion of the waterproof shield element, with a terminal end portion of the flexible elongated projection being, when at rest, curved to extend towards the center of the cavity defined by the waterproof shield element.

5. The apparatus of claim 1, wherein the seal element comprises the at least two projections, and wherein the at least two projections comprise:
   a first projection that extends away from the lower portion of the waterproof shield element, with its respective terminal portion being curved to extend, when at rest, towards the center of the cavity that is defined by the waterproof shield element; and
   a second projection that extends away from the lower portion of the waterproof shield element, with its respective terminal portion extending, when at rest, away from the center of the cavity that is defined by the waterproof shield element.

6. The apparatus of claim 1, wherein an upper portion of the seal element comprise a projection that is mated with a ridge and a cutout at the lower portion of the waterproof shield element.

7. The apparatus of claim 1, wherein an upper portion of the seal element comprise a first projection and a second projection that mate with a ridge and a cutout at the lower portion of the waterproof shield element.

8. The apparatus of claim 1, wherein the seal element comprises the at least two projections, and wherein the at least two projections comprise a first projection, a second projection, and a third projection.

9. The apparatus of claim 8, wherein, when the seal element is at rest, the respective terminal end of each of the first projection, the second projection, and the third projection extend away from the lower portion of the waterproof shield element and away from the center of the cavity that is defined by the waterproof shield element.

10. The apparatus of claim 9, wherein the seal element comprises the at least two projections that each extend away from the lower portion of the waterproof shield element and that each have a respective terminal portion that is configured to contact the user's body when the waterproof shield element forms the effective seal between the waterproof shield element and the user's body, and wherein the respective terminal portion of each of the at least two projections extend away from the center of the cavity defined by the waterproof shield element.

11. The apparatus of claim 1, further comprising an attachment mechanism that is coupled to the waterproof shield element, wherein the retention mechanism comprises a flexible strap having a rod element that is configured to selectively engage a catch of the attachment mechanism.

12. A method for protecting a wound, the method comprising:
   providing a waterproof shield element to cover a wound area of a user's body, the waterproof shield element comprising an elevated top surface that is configured to be elevated away from the user's body during use;
   coupling a seal element to a lower portion of the waterproof shield element, wherein the waterproof shield element comprises at least one of:
   (i) a base portion that is coupled to the lower portion of the waterproof shield element, wherein a first end portion of a flexible elongated projection is coupled to the base portion such that a second end of the flexible elongated projection extends away from the base portion of the seal element and away from the lower portion of the waterproof shield element and towards a center of a cavity defined by the waterproof shield element such that the second end of the flexible elongated projection is configured to extend between the base portion of the seal element and the user's body when the waterproof shield element covers the wound area of the user's body; and
   (ii) at least two projections that each extend away from the lower portion of the waterproof shield element and that each have a terminal portion that is configured to contact the user's body during use; and providing a retention mechanism to selectively retain the waterproof shield element against the user's body during use, the retention mechanism being configured to create, during use, a force between the waterproof shield element and the user's body to form an effective seal between the seal element and the user's body.

13. The method of claim 12, wherein the retention mechanism comprises a flexible strap that is adjustably coupled to an elongated member having a longitudinal axis that runs orthogonal to a length of the flexible strap, wherein the method further comprises coupling an attachment mechanism to the waterproof shield element, and wherein the attachment mechanism is configured to selectively catch the elongated member to secure a position of the retention mechanism relative to the waterproof shield element.

14. The method of claim 12, wherein the seal element comprises the base portion with its flexible elongated projection.

15. An apparatus for protecting a wound, the apparatus comprising:

a waterproof shield element to cover a wound area of a user's body, the waterproof shield element comprising an elevated top surface that is configured to be elevated away from the user's body during use;

a seal element coupled to a lower portion of the waterproof shield element, wherein the seal element comprises:

a first annular, flexible projection that extends away from the lower portion of the waterproof shield element, that extends around a perimeter of the lower portion of the waterproof shield element, that, when at rest, has a curved terminal portion that extends towards a center of a cavity defined by the waterproof shield element, and that is configured to contact the user's body during use; and a second annular, flexible projection that extends away from the lower portion of the waterproof shield element, that extends around the perimeter of the lower portion of the waterproof shield element, that, when at rest, extends away from the center of the cavity defined by the waterproof shield element, and that has a terminal part that is configured to contact the user's body during use; and a retention mechanism to selectively retain the waterproof shield element against the user's body during use, the retention mechanism being configured to create, during use, a force between the waterproof shield element and the user's body to form an effective seal between the seal element and the user's body.

16. The apparatus of claim 15, wherein the retention mechanism comprises a flexible strap that is adjustably coupled to an elongated member having a longitudinal axis that runs orthogonal to a length of the flexible strap, wherein the apparatus further comprises an attachment mechanism that is coupled to the waterproof shield element and that defines a recess, and wherein the recess is configured to selectively catch the elongated member.

17. The apparatus of claim 15, wherein the elevated top surface comprises an attachment element that is coupled with a first end portion of the retention mechanism and a securing element that is configured to selectively couple with a second end portion of the retention mechanism.

* * * * *